United States Patent [19]

Goldenberg

[11] Patent Number: 5,711,309
[45] Date of Patent: Jan. 27, 1998

[54] APPARATUS FOR COLLECTING MIDDLE EAR SPECIMENS

[76] Inventor: Robert A. Goldenberg, 501 Stonehaven Rd., Dayton, Ohio 45429

[21] Appl. No.: 592,589

[22] Filed: Jan. 26, 1996

[51] Int. Cl.⁶ .................................................. A61B 5/00
[52] U.S. Cl. ..................... 128/760; 606/109; 128/765; 128/759
[58] Field of Search .................................. 128/760, 763, 128/766, 765, 754; 604/403, 410, 318; 606/108, 109, 167, 170, 180

[56] References Cited

U.S. PATENT DOCUMENTS

| | | |
|---|---|---|
| 4,175,008 | 11/1979 | White . |
| 4,184,483 | 1/1980 | Greenspan . |
| 4,312,950 | 1/1982 | Snyder et al. . |
| 4,353,868 | 10/1982 | Joslin et al. . |
| 4,641,663 | 2/1987 | Juhn . |
| 4,707,450 | 11/1987 | Nason . |
| 4,760,847 | 8/1988 | Vaillancourt . |
| 4,803,998 | 2/1989 | Kezes et al. . |
| 4,813,432 | 3/1989 | Saint-Amand . |
| 5,053,040 | 10/1991 | Goldsmith, III . |
| 5,078,968 | 1/1992 | Nason . |
| 5,129,402 | 7/1992 | Koll et al. . |
| 5,145,565 | 9/1992 | Kater et al. ........................ 204/153.1 |

*Primary Examiner*—Max Hindenburg
*Assistant Examiner*—Pamela L. Wingood
*Attorney, Agent, or Firm*—Killworth, Gottman, Hagan & Schaeff, L.L.P.

[57] ABSTRACT

The present invention is an apparatus and method for collecting a specimen of middle ear fluid, through the ear drum of a patient, for subsequent culturing. The present invention involves using a needle that is adapted for puncturing through the ear drum, with a fluid absorbent material disposed on the needle to absorb a sufficient specimen of middle ear fluid for subsequent culturing and identification of bacteria present. Such an apparatus can be made inexpensively and disposable after each use. A stop guard can be secured to the needle to inhibit penetration of the needle beyond a desired depth through the ear drum. The stop guard enables the desired depth of penetration, through the ear drum, to be determined without having to rely solely on the skill of the practitioner performing the procedure.

20 Claims, 2 Drawing Sheets

APPARATUS FOR COLLECTING MIDDLE EAR SPECIMENS

FIELD OF THE INVENTION

The present invention is related to the medical procedure of removing fluid specimens (e.g., pus and other secretions) from the middle ear space of a patient, and more particularly to an apparatus for collecting middle ear specimens through the ear drum and preserving the specimen for subsequent culturing.

BACKGROUND OF THE INVENTION

Recent medical studies have found that antibiotic resistant bacterial organisms are becoming more and more prevalent. Most bacterial infections are cultured and the type of bacteria causing the infection identified before an antibiotic treatment is prescribed. Infections of the middle ear (i.e., otitis media) are one of the few bacterial infections which are routinely treated without first being cultured and the bacterial strain identified. In general, without a pre-treatment identification of each bacterial strain present in the infected area, there is a risk that the chosen antibiotic treatment will be ineffectual. This risk has increased with the ever increasing number of antibiotic resistant bacteria. Depending on the type of infection, prescribing an ineffectual treatment can unnecessarily prolong a patient's pain and suffering and may even result in further complications from recurrent otitis media.

One main reason bacterial ear infections are typically not cultured and identified before being treated is because the ability to collect a specimen from the middle ear space has been limited by the equipment and devices previously used for that purpose. One such prior collection system had a handle at one end which was connected to a vacuum pump, a hollow needle at its other end and a vial attached to the handle for collecting aspirated fluid. The needle was inserted through a patient's ear drum (i.e., tympanic membrane) and the vacuum pump was operated to establish a vacuum used to withdraw fluid from the middle ear space and collect the fluid in the vial. One problem with this type of collection system is the need for an external vacuum pump. Such mechanical vacuum pumps are expensive and not always available when and where needed, for example, in many less developed countries and under served areas of even major industrialized countries. Because some type of tubing and connector is needed to connect the specimen aspirator to the external vacuum pump, this type of collection system can be cumbersome and unwieldy, making it difficult to collect a specimen of middle ear fluid.

A collection apparatus which does not require an external vacuum source is disclosed in U.S. Pat. No. 4,641,663. This collector is a hypodermic needle assembly with a plunger which is spring loaded to draw fluid through its hollow needle once a latch mechanism is released. While it is self-contained (i.e., does not use an external suction pump or vacuum source) and disposable, this specimen aspirator is still relatively complex and, thus, expensive to manufacture. A problem shared by both of the above described prior specimen collection systems is that the depth of penetration by the hollow needle, into the middle ear space, is largely dependent on the skill and experience of the person performing the procedure. Thus, the use of either of these devices is likely to be limited to only the most experienced practitioners.

Therefore, especially with the apparent continued proliferation of antibiotic resistant bacteria, there is an increasing need for a disposable and inexpensive apparatus for collecting a fluid specimen from the middle ear space of a patient without the need of an external vacuum source (i.e., self-contained). There is a further need for such an apparatus which does not rely solely on the practitioner's skill to determine the depth of penetration through the ear drum.

SUMMARY OF THE INVENTION

These needs are met by providing an apparatus and method, according to the principles of the present invention, for collecting a middle ear fluid specimen through the ear drum of a patient. Broadly, the present invention involves using a needle that is adapted for puncturing the ear drum. A fluid absorbent material is secured to the needle so as to absorb a specimen of middle ear fluid, when disposed through the ear drum. Such an apparatus can be made inexpensively and disposable after each use. The present invention eliminates the need of using relatively complex structure for producing a vacuum, such as an external vacuum source, to obtain a specimen of middle ear fluid.

In one aspect of the present invention, an apparatus is provided which comprises such a needle and fluid absorbent material. One possible feature of the present apparatus is a stop guard that is secured to the outside of the needle. The stop guard is adapted to inhibit penetration of the needle beyond a desired depth through an ear drum. That is, once the desired depth through the ear drum is reached, the stop guard provides enough resistance to further penetration that a practitioner can tell that the desired depth has been reached. Thus, with this feature, the depth of penetration through the ear drum can be determined without having to rely solely on the skill of the practitioner performing the procedure.

It may be desirable for the collected middle ear specimen to be kept in a specimen collection container. The specimen collection container can be any structure suitable for keeping the collected specimen in condition for subsequent culturing and identification (e.g., a test tube, a sheath suitable for receiving and being secured to the needle, etc.). It may be desirable for the specimen collection container to include a preservative (i.e., any suitable medium for keeping bacteria in the specimen viable for subsequent culturing and identification). The preservative can be simply deposited within the specimen container or separately packaged therewithin. For example, the preservative can be disposed in a package that is puncturable by the needle. Alternatively, the specimen container can be formed with a flexible wall, and the preservative can be disposed in a package that is breakable by flexing the flexible wall.

The fluid absorbent material can be disposed on the outside of the needle between its distal and proximal ends. Alternatively, when the needle has a hollow section with a tubular wall and an opening leading to the hollow section, the fluid absorbent material can be disposed inside the hollow section. The opening to the hollow section can be formed at the distal end of the needle or through the wall of the hollow section on the side of the needle. For ease of manufacturing, when the needle includes such a hollow section, the length of the needle can be made hollow. It may be desirable for such a hollow needle to be connectable to an external suction or vacuum source (e.g., an external vacuum pump) in order to draw middle ear fluid into the fluid absorbent material. The costly external vacuum source can be reused while the relatively inexpensive needle of such an apparatus can be disposable.

A middle ear specimen can also be collected for culturing and identification, according to the present invention, by making the needle at least partially hollow at its distal end and forming one or more perforations through its tubular wall, with the one or more perforations being in fluid communication with the opening leading to the hollow section. With such an embodiment, the fluid absorbent material is either disposed on the outside or on the inside of the hollow section adjacent to the perforations so as to absorb at least part of a fluid specimen through one or more such perforations. When the needle includes a stop guard, it is desirable for the one or more perforations to be disposed between the stop guard and distal end of the needle.

The needle can include a flared portion at its distal end to protect the fluid absorbent material from having portions of the absorbing material dislodged while the distal end of the needle is forced through and removed from an ear drum. This portion is flared so as to be generally flush with or extend radially out beyond the outer surface of the absorbent material. The fluid absorbent material is disposed behind the flared portion of the needle.

In another aspect of the present invention, a method is provided comprising the steps of: providing a needle as described above; inserting the needle through the ear drum of a patient; absorbing a specimen of middle ear fluid into the fluid absorbent material; and withdrawing the needle from the ear of the patient. The present method can further comprise the step of directing the specimen into a specimen collection container with a preservative contained therein. The present method can also further comprise the step of puncturing a package containing the preservative, with the needle. With the above described stop guard being secured to the needle, the step of inserting the needle through the ear drum includes inserting the needle up to the stop guard. With the needle having at least one perforation as described above, the step of allowing a specimen of middle ear fluid to be absorbed includes absorbing a specimen of middle ear fluid into the fluid absorbent material through one or more such perforations.

The objectives, features, and advantages of the present invention are apparent upon consideration of the present specification and the appended drawings.

DETAILED DESCRIPTION OF THE INVENTION

Figure 1:
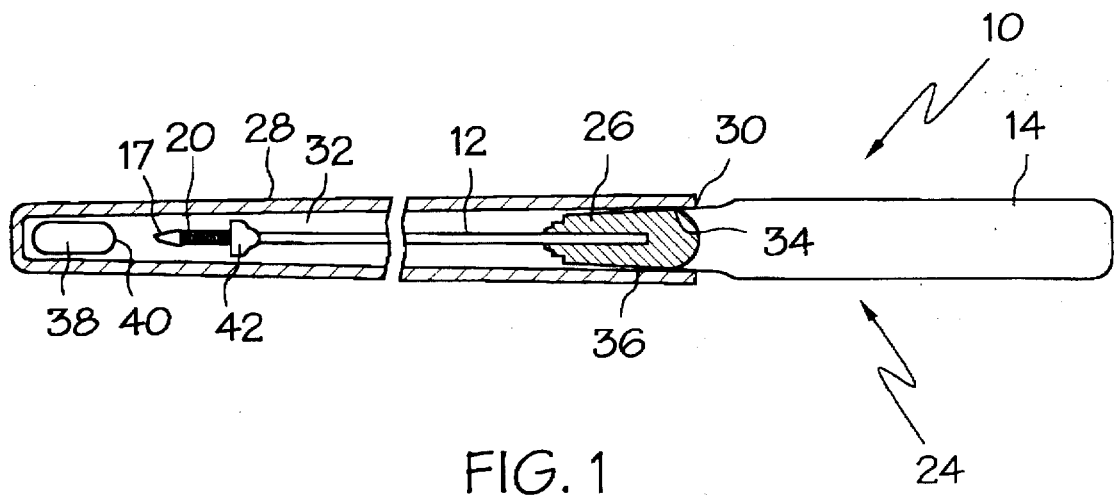
FIG. 1 is a partially broken-away sectional view of one embodiment of the present apparatus for collecting a middle ear fluid specimen through the ear drum of a patient, including a specimen collection container.

Although the present invention is herein described in terms of specific embodiments, it will be readily apparent to those skilled in this art that various modifications, re-arrangements, and substitutions can be made without departing from the spirit of the invention. The scope of the present invention is thus only limited by the claims appended hereto.

An apparatus 10, according to the present invention, broadly includes a needle 12 mounted on a handle 14. The needle 12 has a distal end 16 with a pointed tip 17, for puncturing through the ear drum 18 of a patient (see FIG. 2). The needle 12 can be straight or formed with a desired bend (see FIGS. 1 and 2, respectively) and is sufficiently long to reach and penetrate the ear drum 18. A fluid absorbent material 20 is secured to the needle 12 so as to absorb a specimen of middle ear fluid 22, when disposed through the ear drum 18. The fluid absorbent material 20 may include, for example, one or a combination of cotton, cotton-wool and calcium alginate, to name a few.

Referring to FIG. 1, in one embodiment of apparatus 10, generally designated by the reference numeral 24, the needle 12 is straight and the handle 14 includes a hub 26 that mounts the proximal end of the needle 12. The hub 26 can be an integral part of the handle 14 (as shown) or removably mounted to the handle 14. The hub 26 is adapted to be secured to a specimen container 28 used to store the specimen of middle ear fluid 22, collected by the absorbent material 20, for subsequent culturing.

The specimen container 28, for example, can be in the form of a sheath, similar to those used to protect conventional hypodermic needles. The sheath 28 has an opening 30 leading to a containment chamber 32. The specimen of fluid 22 is stored in the container 28 by disposing the needle 12 through the opening 30 and into chamber 32. The sheath 28 can be adapted to receive the full length of the needle 12 and so that the hub 26 seats inside the opening 30, for example, with an interference or press fit. It is desirable to keep the opening 30 of the specimen container 28 closed until the specimen can be cultured, to prevent the specimen from being inadvertently lost or contaminated. Therefore, it may be desirable for the hub 26 and the container 28 to be connected to one another more securely than by using an interference or press fit, to insure that a sterile non-contaminated environment is maintained around the specimen of middle ear fluid 22. A threaded connection, a luer-lock connection or any other more secure connecting system can be used to removably connect together the hub 26 and the container 28. For example, the mating surfaces 34 and 36 of the container opening 30 and the hub 26, respectively, can be formed with threads and threadably engaged, rather than press fit together.

It may be desirable to use a preservative 38 which is suitable for preserving the specimen of middle ear fluid 22 in condition for subsequent culturing and identification. The preservative 38 may be, for example, a liquid such as distilled water, saline solution, or other non-reactive liquid which will provide an environment in which the bacteria will remain viable for subsequent culturing. The preservative 38 may also be one or a combination of Stuart's Medium, Bartel's Biotransport Medium and thioglycollate. The preservative 38 can be unconstrained and free to move about within the chamber 32. However, to prevent the likelihood of spillage, it is desirable for the preservative 38 to be kept constrained within a separate package 40, such as the frangible ampoule disclosed in U.S. Pat. No. 3,450,129, which is incorporated herein by reference in its entirety. When the preservative 38 is kept in such a frangible ampoule 40, it is desirable for the wall of the container 28 to be collapsible in order to fracture the ampoule 40 and release the liquid preservative 38. The package 40 containing the preservative 38 can also be made puncturable, by the pointed tip 17 of the needle 12, to effect the release of the preservative 38.

Figure 2:
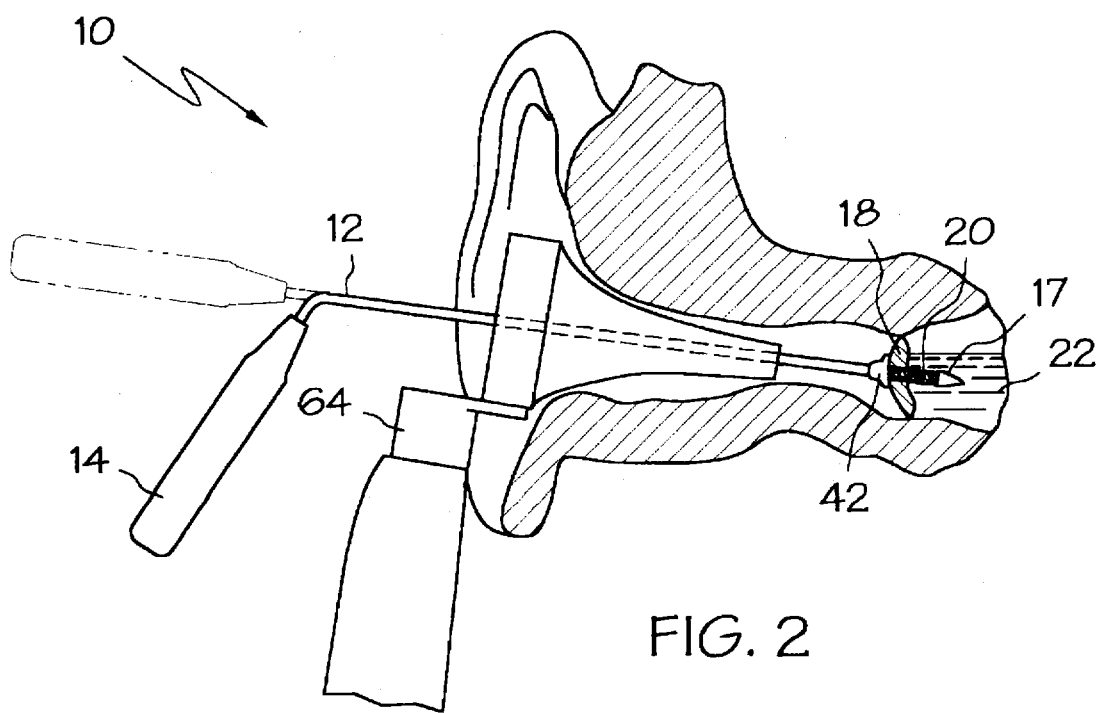
FIG. 2 is a side view of another embodiment of the present apparatus in position to collect a fluid specimen, with the ear of a patient shown in cross-section.

It is desirable for a stop guard 42 to be mounted or otherwise disposed on the needle 12 to inhibit penetration of the needle 12 beyond a desired depth through the ear drum 18 (see FIG. 2). That is, once the desired depth through the ear drum 18 is reached, the stop guard 42 provides enough resistance to further penetration that a practitioner handling the apparatus 10 can tell that the desired depth has been reached. Thus, the depth of penetration through the ear drum 18 can be determined without having to rely solely on the skill of the practitioner performing the procedure.

It is believed that a number of suitable designs for the stop guard 42 are feasible. For example, the stop guard 42 can be a ring formed around the outside of the needle 12. The ring shaped stop guard 42 can be bell shaped (see FIGS. 1, 2 and 5), washer-shaped (see FIG. 3), cone-shaped (see FIG. 4) or any other suitable configuration. It is desirable for the stop guard 42 to be bonded or otherwise fixed at a desired location on the needle 12. To this end, the stop guard 42 can be manufactured as an integral part of the needle 12. For example, the stop guard 42 can be formed along with the needle 12, such as when both are molded using a plastic material. The stop guard 42 can also be welded in place to the needle 12, such as when they are both made of a metal. Alternatively, it may be desirable to make the location of the stop guard 42, on the needle 12, adjustable. This adjustability can be obtained by making the stop guard 42 with an inside diameter that forms an interference or press fit when slipped over the needle 12. Such a stop guard 42 can be made adjustable and still sufficiently inhibit further penetration of the needle 12 through the ear drum 18 by adjusting the strength of the interference or press fit (i.e., varying the inside diameter of and/or the material used to make the stop guard 42).

Figure 3:
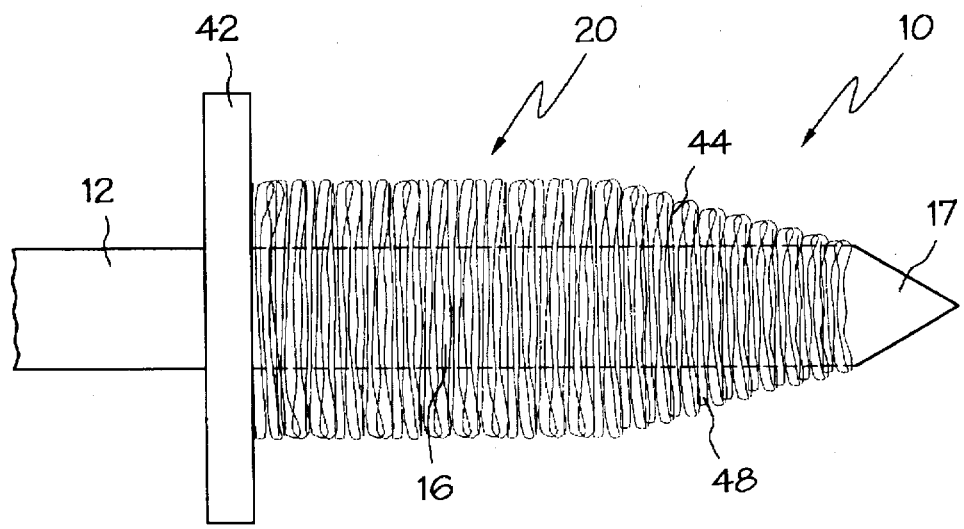
FIG. 3 is an enlarged side view of one embodiment of a distal end of a needle used to form part of an apparatus of the present invention.

The fluid absorbent material 20 can be, for example, in the form of fibers 44 wrapped around the distal end 16 of the needle 12 (see FIG. 3). The material 20 can also be in the form of a fibrous mat 46 disposed inside or outside the distal end 16 of the needle 12 (see FIGS. 4 and 5, respectively). It is understood that the present invention is not intended to be so limited. The fluid absorbent material 20 can include any suitable material and have any suitable form for absorbing middle ear fluid. It is important that the fluid absorbent material 20 be able to not only absorb a sufficient amount of middle ear fluid 22 but also enable any bacteria present in the absorbed specimen to be subsequently cultured and identified.

Referring to FIG. 3, the needle 12 of an apparatus 10 can have a uniform cross-section up to its pointed tip 17. With the pointed tip 17 being conically-shaped (as shown), it may be desirable for its fluid absorbing material 20 to be disposed on the outside of the distal end 16 with at least a leading portion 48 tapered so as to form a gradual transition between the pointed tip 17 and the material 20.

Figure 4:
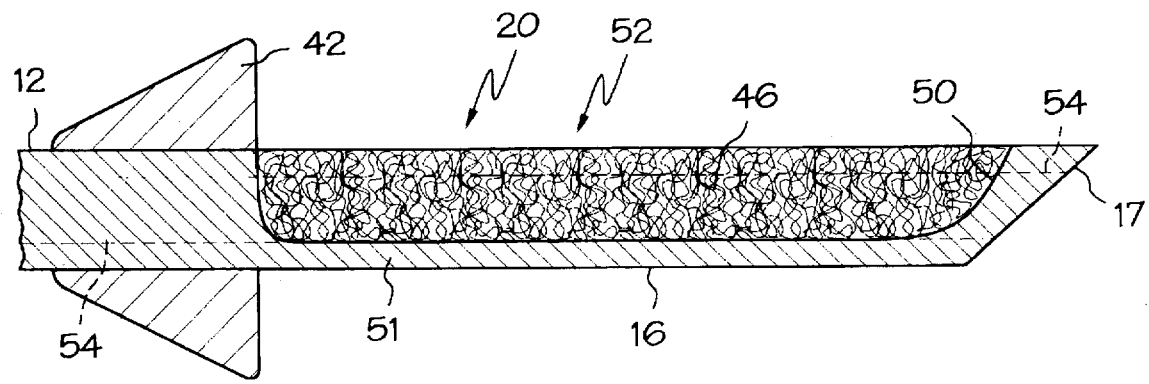
FIG. 4 is an enlarged sectional view of another embodiment of a distal end of a needle used to form part of an apparatus of the present invention.

In addition, referring to FIG. 4, the needle 12 of an apparatus 10 can have a hollow section 50 formed by a wall 51 and an access opening 52 leading to the hollow section 50. The mat 46 of fluid absorbent material 20 is disposed inside the hollow section 50 through the opening 52. The opening 52 provides a path through which middle ear fluid 22 can reach and be absorbed by the fluid absorbing material 20. For ease of manufacturing, the hollow section 50 can be formed by making the length of the needle 12 hollow (indicated with phantom lines 54). Accordingly, the opening 52 leading to the hollow section 50 can be formed through the wall 51 on the side of the needle 12 (as shown) and/or through its tip 17 (as shown in phantom). It may be desirable for the hollow needle 12 to be operatively adapted so as to be connectable to external suction or vacuum source, such as a conventional medical vacuum pump, in order to draw middle ear fluid into the fluid absorbent material.

Figure 5:
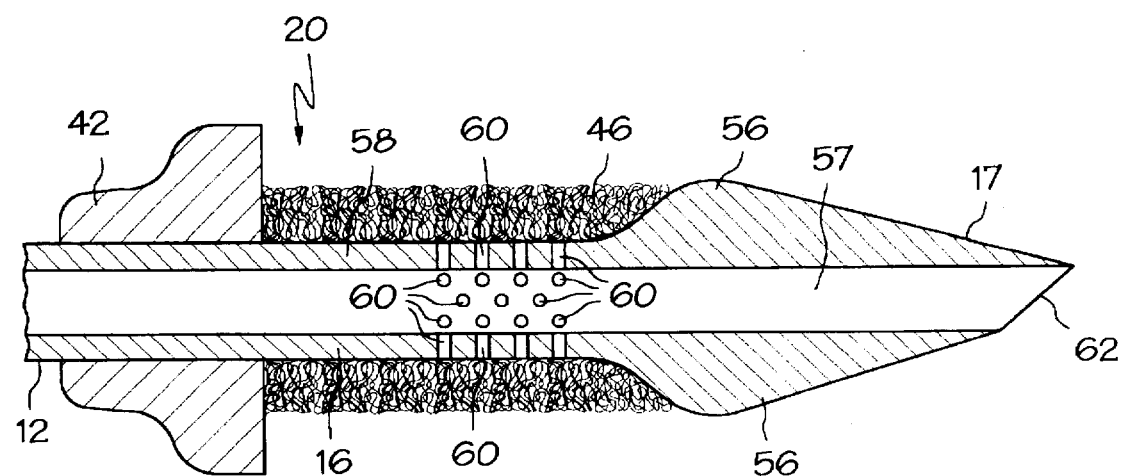
FIG. 5 is an enlarged sectional view of an additional embodiment of a distal end of a needle used to form part of an apparatus of the present invention.

Furthermore, referring to FIG. 5, the pointed tip 17 of the needle 12 of an apparatus 10 can include a flared portion 56 to protect the fluid absorbent material 20 from having portions of the absorbing material 20 dislodged while the distal end 16 of the needle 12 is forced through and removed from an ear drum 18. The fluid absorbent material 20 is disposed behind the flared portion 56 of the needle 12, and this portion 56 is flared so as to be generally flush with or extend radially out beyond the outer surface of the absorbent material 20. Thus, whenever the fluid absorbent material 20 is disposed on the outside of the needle, it may be desirable for the tip 17 of the needle 12 to include a flared portion 56, regardless of whether the needle is hollow (like that shown in FIG. 5) or solid (like that shown in FIG. 3).

Also referring to FIG. 5, the needle 12 of an apparatus 10 can have a hollow section 57 formed along at least part of its distal end 16 (e.g., by using a hypodermic needle for the needle 12), with a tubular wall 58 and one or more perforations 60 formed through its tubular wall 58. The perforations 60 are in fluid communication with an opening 62 formed through the tip 17. The fluid absorbent material 20 can be disposed on the outside (as shown) of the tubular wall 58 adjacent to the perforations 60. When the absorbing material 20 is so disposed on the outside of the perforated tubular wall 58, more surface area of the absorbing material 20 is available for absorbing middle ear fluid 22. The underside of the material 20 can absorb middle ear fluid 22 present in the hollow section 57 through one or more of the perforations 60, and the outer surface of the material 20 can absorb fluid 22 it comes in direct contact with. By increasing the surface area of material 20 exposed to fluid 22, the amount of fluid 22 collected by the absorbent material 20 can also be increased. When the needle 12 includes a stop guard 42, the perforations 60 are disposed on the distal end 16 of the needle 12, in front of the stop guard 42. It may also be desirable, with this embodiment, to draw middle ear fluid 22 into the hollow section 57 using an external vacuum or suction source, such as a conventional medical vacuum pump, connected to the proximal end of the hollow needle 12.

Referring to FIG. 2, during the collection of a specimen of middle ear fluid 22 according to the present invention, it is desirable to use a conventional otoscope 64 with any embodiment of apparatus 10. In one method for collecting a specimen of middle ear fluid 22, the otoscope 64 is inserted into the patient's ear and used to locate the ear drum 18. The needle 12 is then inserted through the otoscope 64 and the distal end 20 is forced through the ear drum 18 until the stop guard 42 makes contact with the ear drum 18. To help ensure that the fluid absorbent material 20 contacts and absorbs a sufficient amount of middle ear fluid 22, it may be desirable to rotate the needle 12 slightly, about its longitudinal axis. The needle 12 is then withdrawn from the patient's ear. The distal end 20 of the needle 12 can then be inserted into a specimen container 28 through its opening 30, and the opening 30 is then closed, for example, as described above. The preservative 38 is then freed from its package 40, as describe above, and allowed to saturate the absorbent material 20. The collected specimen of middle ear fluid 22 is now ready for subsequent culturing to identify the bacteria present in the patient's middle ear, using conventional culturing and identification techniques.

From the above disclosure of the general principles of the present invention and the preceding detailed description, those skilled in this art will readily comprehend the various modifications to which the present invention is susceptible. Therefore, the scope of the invention should be limited only by the following claims and equivalents thereof.

What is claimed is:

1. An apparatus for collecting a middle ear fluid specimen through the ear drum of a patient, said apparatus comprising:
   a needle having a distal end adapted for puncturing through the ear drum of a patient; and
   a fluid absorbent material disposed on said needle and operatively adapted to absorb a specimen of middle ear fluid.

2. The apparatus as set forth in claim 1, wherein needle has a proximal end, and said fluid absorbent material is disposed on the outside of said needle between said distal end and said proximal end.

3. The apparatus as set forth in claim 1, further comprising a stop guard secured to the outside of said needle a desired distance from said distal end, said stop guard being adapted to inhibit further penetration of said needle through an ear drum.

4. The apparatus as set forth in claim 1, further comprising a specimen container having an opening adapted for allowing the distal end of said needle therethrough and containing a preservative for preserving a middle ear specimen collected by said fluid absorbent material.

5. The apparatus as set forth in claim 4, wherein said preservative is in a package that is puncturable by said needle.

6. The apparatus as set forth in claim 4, wherein specimen container has a flexible wall and said preservative is in a package that is breakable by flexing said flexible wall.

7. The apparatus as set forth in claim 1, wherein said needle has a hollow section with a tubular wall and an opening to said hollow section, and said fluid absorbent material is disposed at least one of inside and outside said hollow section.

8. The apparatus as set forth in claim 7, wherein said opening to said hollow section is formed at said distal end.

9. The apparatus as set forth in claim 7, wherein said opening to said hollow section is formed through said tubular wall, on the side of said needle.

10. The apparatus as set forth in claim 7, wherein said needle is a hollow needle.

11. The apparatus as set forth in claim 10, further comprising an external vacuum source connected to said hollow needle so as to draw middle ear fluid into said fluid absorbing material.

12. The apparatus as set forth in claim 1, wherein said needle has a hollow section with a tubular wall at said distal end, said tubular wall has at least one perforation formed therethrough and in fluid communication with an opening to said hollow section at said distal end, and said fluid absorbent material is disposed on at least one of the outside of and inside said hollow section adjacent to said at least one perforation.

13. The apparatus as set forth in claim 12, further comprising a stop guard secured to said needle a desired distance from said opening to said hollow section, said stop guard being adapted to inhibit further penetration of said needle through an ear drum, and said at least one perforation is disposed between said stop guard and said opening.

14. The apparatus as set forth in claim 1, wherein said needle includes a flared portion at said distal end, and said fluid absorbent material is disposed behind said flared portion.

15. A method for collecting a middle ear fluid specimen through the ear drum of a patient, said method comprising the steps of:
   providing a needle with a distal end adapted for puncturing through the ear drum of a patient, and a fluid absorbent material disposed on the needle and operatively adapted to absorb a specimen of middle ear fluid;
   inserting the needle through the ear drum of a patient;
   absorbing a specimen of middle ear fluid into the fluid absorbent material; and
   withdrawing the needle from the ear of the patient.

16. The method as set forth in claim 15, further comprising the step of directing the specimen into a specimen collection container with a preservative contained therein.

17. The method as set forth in claim 15, further comprising the step of puncturing a package containing the preservative with the needle.

18. The method as set forth in claim 15 wherein the needle being provided has a stop guard secured thereto, and said step of inserting the needle through the ear drum includes inserting the needle up to the stop guard.

19. The method as set forth in claim 15, wherein the needle being provided has a hollow section, with a tubular wall defining an opening at the distal end, and at least one perforation formed therethrough, and said step of allowing a specimen of middle ear fluid to be absorbed includes absorbing a specimen of middle ear fluid into the fluid absorbent material through the at least one perforation.

20. The method as set forth in claim 15, wherein the needle being provided is a hollow needle, and said method further comprises the step of drawing middle ear fluid into the fluid absorbing material by connecting the hollow needle to an external vacuum source.

* * * * *